(12) United States Patent
Wiese

(10) Patent No.: US 8,043,636 B2
(45) Date of Patent: Oct. 25, 2011

(54) ORGANIC HERBICIDE AND METHOD FOR MANUFACTURING

(75) Inventor: Lars Ole Wiese, Løkken (DK)

(73) Assignee: VegaNo ApS, Løkken (DK)

( * ) Notice: Subject to any disclaimer, the term of this patent is extended or adjusted under 35 U.S.C. 154(b) by 415 days.

(21) Appl. No.: 12/309,590

(22) PCT Filed: Jul. 3, 2007

(86) PCT No.: PCT/DK2007/000335
§ 371 (c)(1), (2), (4) Date: Mar. 9, 2009

(87) PCT Pub. No.: WO2008/011882
PCT Pub. Date: Jan. 31, 2008

(65) Prior Publication Data
US 2009/0197766 A1   Aug. 6, 2009

(30) Foreign Application Priority Data
Jul. 27, 2006 (DK) .................. 2006 01016

(51) Int. Cl.
*A61K 36/8962* (2006.01)
*A61K 36/81* (2006.01)
*A61K 36/00* (2006.01)

(52) U.S. Cl. .............. 424/754; 424/760; 424/725

(58) Field of Classification Search .................. None
See application file for complete search history.

(56) References Cited

U.S. PATENT DOCUMENTS

| | | | |
|---|---|---|---|
| 5,756,100 A | 5/1998 | Martinez | |
| 6,299,867 B1* | 10/2001 | Aoyagi et al. | 424/76.1 |
| 6,352,713 B1* | 3/2002 | Kirschner et al. | 424/441 |
| 6,579,543 B1* | 6/2003 | McClung | 424/728 |
| 2005/0281792 A1* | 12/2005 | Short et al. | 424/93.45 |
| 2006/0194698 A1* | 8/2006 | Gwinn et al. | 504/117 |
| 2007/0274956 A1* | 11/2007 | Shibata et al. | 424/93.5 |

FOREIGN PATENT DOCUMENTS

| | | |
|---|---|---|
| CN | 1541540 | 11/2004 |
| CN | 1582671 | 2/2005 |
| CN | 1666618 | 9/2005 |
| JP | 6321672 | 11/1994 |
| WO | 2004062370 | 7/2004 |

OTHER PUBLICATIONS

English Abstract of JP632.1672, 1994.
English Abstract of CN1582671, 2005.
English Abstract of CN1666618, 2005.
English Abstract of CN 1541540, 2004.
English Abstract of CN1541540, 2004.
Kadioğlu et al., "Allelopathic Effects of Plant Extracts Against Seed Germination of Some Weeds" in Asian Journal of Plant Sciences, vol. 3, No. 4, pp. 472-475 (2004).

* cited by examiner

*Primary Examiner* — Christopher R. Tate
(74) *Attorney, Agent, or Firm* — Dykema Gossett pLLC

(57) ABSTRACT

An organic agent for controlling weeds (a so-called herbicide) primarily includes ingredients which are used for human nutrition and the individual components are harmless to nature (including animals and people). These ingredients include extract of garlic, cayenne pepper, nettles and sugar in the form of dextrose. Thorough tests have documented that the new organic herbicide has the same efficiency or is better than one of the hitherto most-used chemical herbicides.

5 Claims, No Drawings

ORGANIC HERBICIDE AND METHOD FOR MANUFACTURING

BACKGROUND OF THE INVENTION

1. Field of the Invention

The invention relates to a herbicide agent for controlling weeds, where the herbicide agent includes extract from the plants garlic, cayenne pepper, nettles and sugar including dextrose.

Moreover, the invention relates to a method of manufacturing herbicide based on natural non-chemical substances, where garlic juice, cayenne pepper, nettle juice, dextrose, vinegar, lime water, silicon and water are mixed in a tub or a tank and stirred for 1 to 3 hours, preferably 2 hours, after which the mixed liquid settles for 10 to 100 hours, preferably 24 hours, following which the mixture is racked off and sieved.

2. The Prior Art

Herbicide agents for controlling weeds are known and are used in a still increasing extent.

The hitherto best-known herbicide agents for weed control or so-called herbicides are based on chemical materials, which have been developed especially for the purpose.

The spreading of the known chemical herbicides intensified from the beginning of the previous century, primarily initiated by the new technological possibilities of that era, which the chemicals industry could make use of.

It has been found, however, that the known herbicides involve some drawbacks.

Several research results have thus proven that many of the chemical substances used for herbicides have negative consequences on nature including animals and people.

So there are numerous examples of scientifically substantiated proof of the harmful effects of the used chemical substances on, e.g., the drinking water, food products, the fertility of animals and people and occurrence of cancer etc.

Since the negative effects of the used chemical substances are often first visible after many years of use, the negative consequences from use of the substances can become even greater than it is currently admitted.

A product to be used for controlling weeds is known from JP 6321672 A, where the product comprises herb extracts, for example garlic juice and fruits of capsicum annum. Such products are not known to have the same effect as the most-used chemical herbicides.

It is therefore a purpose of the invention to improve herbicide agents for controlling weeds, so that a more efficient herbicide agent is achieved, which has the same effect as the hitherto most-used chemical herbicides.

SUMMARY OF THE INVENTION

The object of the invention is achieved by a herbicide agent includes garlic extracts, cayenne pepper extracts, nettles and sugar (including dextrose), as well as the ingredients vinegar, lime including lime water, silicon and water, in that the agent consists of a mixture which in terms of volume preferably consists of:
Garlic juice (5 to 50%)
Cayenne pepper (1 to 10%)
Nettle juice (1 to 10%)
Dextrose (1 to 10%)
Vinegar (1 to 10%)
Lime water (1 to 10%)
Silicon (0.5 to 5%)
Water (50 to 90%)

An appropriate mixture of the described natural substances, which are commonly known food products, achieves the surprising effect that the mixture of substances can efficiently control weeds.

Tests have shown that addition of the described natural substances in a mixture in terms of the preferred volume increases the efficiency of the new herbicide agent.

In this way, it thus becomes possible to completely avoid the use of chemical agents and thereby avert that nature including animals and human beings are affected by unknown risks.

By addition of the latter mentioned natural substances, the surprising result is achieved, that the new herbicide, which can be organic, has the same effect as the hitherto most-used chemical herbicide.

As mentioned the invention also relates to a method of manufacturing herbicide agents based on natural non-chemical substances, where garlic juice, cayenne pepper, nettle juice, dextrose, vinegar, lime water, silicon and water are mixed in a tub or a tank and stirred for 1 to 3 hours, preferably 2 hours, after which the mixed liquid settles for 10 to 100 hours, preferably 24 hours, following which the mixture is racked off and sieved.

This method is characterized in that the listed ingredients are mixed in a ratio that in relation to the final product has the following percentage-wise composition in terms of volume:
Garlic juice (5 to 50%, preferably 20%)
Cayenne pepper (1 to 10%, preferably 2%)
Nettle juice (1 to 10%, preferably 2.5%)
Dextrose (1 to 10%, preferably 5%)
Vinegar (1 to 10%, preferably 4%)
Lime water (1 to 10%, preferably 3%)
Silicon (0.5 to 5%, preferably 1.2%)
Water (50 to 90%, preferably 62.3%).

Hereby it thus becomes possible to simply, efficiently and inexpensively manufacture a non-chemical herbicide based on naturally occurring substances in the necessary quantities.

Test of the present invention is documented in the report (ref. A)
Final report
GEP Report
To evaluate the new product "Vega Mild" for doseresponse
Targets: Stemme, Vioar, Matin, Verss, Vioar and other broadleaved species
and also Agrre, Poann and other grasses.
Trail series: 06HER-03-01
LRØ Planteavlsforsøg
Niels Finsensvej 20
7100 Vejle
Denmark The report is accessible via the Internet at www.vegano.dk.

The invention is created by systematic tests of the herbicide effect of chosen organic substances.

It is thus via these systematic series of experiments that the surprising effect of a special combination of specific organic substances was identified.

The tests have thus shown that extract of the food products garlic, cayenne pepper, nettles and sugar including dextrose in an appropriate mixture ratio has a remarkable effect as herbicide.

In an expanded series of experiments, where several natural substances were added in varying concentrations, it appeared that addition of vinegar, lime including lime water, silicon and water optimized the herbicide effect of the new organic agent.

As documented in the ref. A the new organic herbicide, in a preferred embodiment with empirically determined optimized mixture ratios, has an effect, which is close to or better than the efficiency of the chemical reference herbicide used under the tests.

As mentioned, one of the basic agents in the new organic herbicide is extract of garlic, so-called garlic juice (Latin: allium sativum).

The garlic juice is manufactured by use of granulated or pulverized, for example ground, dried flakes of garlic, which are mixed with water.

In a preferred embodiment, the mixture ratio is 1 kg of pulverized garlic flakes to 16 liters of water.

The mixture of pulverized or granulated garlic flakes and water then settles in a period from 14 days to 60 days, preferably 28 days, during daily stirring.

Hereafter the garlic juice is ready for further application.

Another basic agent is cayenne pepper (Latin: capsicum frutescens).

Cayenne is used in the widely available powder form in which it is also used as spice for food products.

The ingredient nettle juice (Latin: urtico dioica) is manufactured of fresh leaves of nettle, which are finely chopped and mixed with water.

In a preferred embodiment, 1 kg of finely chopped leaves of nettle are mixed with between 3 to 10 liters of water, preferably 6.25 liters of water.

The mixture of finely chopped nettles and water then subsequently settles for 14 to 60 days, preferably 28 days, during daily stirring.

Hereafter, the nettle parts are removed by use of a sieve and the nettle juice is ready for further use.

The ingredient dextrose (Latin: glukose) is used in the commonly known pulverized form, which is also used for food products.

Vinegar (Latin: vinum-agre) is used in a so-called 12% solution, which has been double filtered in advance of its use.

As mentioned, lime water is also an agent (Latin: calcium-hydracid aqua).

The lime water is manufactured by mixture of so-called slaked lime in water in a mixture ratio comparable to 1 kg of lime and between 5 to 10, preferably 7 liters of water.

The mixture of lime and water is mixed thoroughly and settles between 10 to 50 hours, preferably 24 hours, whereafter the precipitated lime is filtered out and the remaining lime water is ready for further application.

Silicon (Latin: amorfsio2—acetice-acid) is used pulverized.

Water (Latin: aqua) is used as ordinary drinking water.

The finished organic herbicide is manufactured on the basis of the previously mentioned ingredients in a preferred embodiment by mixing the ingredients in a tank according to a mixture ratio in terms of volume equivalent to:

Garlic juice (5 to 50%, preferably 20%)
Cayenne pepper (1 to 10%, preferably 2%)
Nettle juice (1 to 10%, preferably 2.5%)
Dextrose (1 to 10%, preferably 5%)
Vinegar (1 to 10%, preferably 4%)
Lime water (1 to 10%, preferably 3%)
Silicon (0.5 to 5%, preferably 1.2%)
Water (50 to 90%, preferably 62.3%)

The mixture is subsequently stirred between 1 to 3 hours, preferably 2 hours, whereafter the mixed liquid settles for 10 to 100 hours, preferably 24 hours, whereafter the mixture is racked off and sieved.

The new organic herbicide is hereafter ready for use.

As it will appear from ref. A the efficiency of the new organic herbicide is surprising, since it is equal to or better than the chemical reference herbicide used in the test.

The new product can thus to a high extent replace the hitherto known chemical herbicides and benefit the environment including animals and people.

The invention claimed is:

1. An herbicide agent for controlling weeds comprising extracts from the plants garlic, cayenne pepper, and nettles, dextrose, vinegar, lime water, silicon, and water, wherein the agent is a mixture in volume % of:
   Garlic juice, 5-50%;
   Cayenne pepper extract, 1-10%;
   Nettle juice, 1-10%;
   Dextrose, 1-10%;
   Vinegar, 1-10%;
   Lime water, 1-10%;
   Silicon, 0.5-5%; and
   Water, 50-90%.

2. The herbicide agent according to claim 1, where the agent consists of:
   Garlic juice, 20%;
   Cayenne pepper extract, 2%;
   Nettle juice, 2.5%;
   Dextrose, 5%;
   Vinegar, 4%;
   Lime water, 3%;
   Silicon, 1.2%; and
   Water, 62.3%.

3. The herbicide agent according to claim 2, wherein said ingredients are organic.

4. A method of manufacturing an herbicide agent based on natural substances, the method comprising mixing garlic juice, cayenne pepper extract, nettle juice, dextrose, vinegar, lime water, and water in a tub or tank and stirring for 1-3 hours, letting the stirred mixture settle for 10-100 hours, then racking off and sieving the settled mixture, wherein the mixture comprises the following volume % of ingredients:
   Garlic juice, 5-50%;
   Cayenne pepper extract, 1-10%;
   Nettle juice, 1-10%;
   Dextrose, 1-10%;
   Vinegar, 1-10%;
   Lime water, 1-10%;
   Silicon, 0.5-5%; and
   Water, 50-90%.

5. The method according to claim 4, wherein said ingredients are organic.

* * * * *